US009480470B2

(12) United States Patent
Roberts

(10) Patent No.: US 9,480,470 B2
(45) Date of Patent: Nov. 1, 2016

(54) SUSPENSION/RETRACTION DEVICE FOR SURGICAL MANIPULATION

(71) Applicant: Yale University, New Haven, CT (US)

(72) Inventor: Kurt Eric Roberts, New Haven, CT (US)

(73) Assignee: Yale University, New Haven, CT (US)

( * ) Notice: Subject to any disclaimer, the term of this patent is extended or adjusted under 35 U.S.C. 154(b) by 237 days.

(21) Appl. No.: 14/338,060

(22) Filed: Jul. 22, 2014

(65) Prior Publication Data

US 2015/0045611 A1    Feb. 12, 2015

Related U.S. Application Data

(63) Continuation of application No. 12/733,095, filed as application No. PCT/US2008/009530 on Aug. 8, 2008, now Pat. No. 8,827,891.

(60) Provisional application No. 61/060,970, filed on Jun. 12, 2008, provisional application No. 60/964,319, filed on Aug. 10, 2007.

(51) Int. Cl.
*A61B 17/02* (2006.01)
*A61B 17/00* (2006.01)
(Continued)

(52) U.S. Cl.
CPC ..... *A61B 17/0218* (2013.01); *A61B 17/00234* (2013.01); *A61B 18/14* (2013.01);
(Continued)

(58) Field of Classification Search
CPC ................... A61B 17/00234; A61B 17/0218; A61B 2017/0225; A61B 2017/0464; A61B 2017/00283
See application file for complete search history.

(56) References Cited

U.S. PATENT DOCUMENTS 5,242,456 A    9/1993  Nash et al.
5,337,736 A *  8/1994  Reddy ................ A61B 17/0218
                                              128/898

(Continued)

FOREIGN PATENT DOCUMENTS

WO   WO 2005/104927    11/2005
WO   WO 2007/136683    11/2007

(Continued)

OTHER PUBLICATIONS

Romanelli et al., Single Port Laparoscopic Cholecystectomy With the Triport System: A Case Report, Surgical Innovation, vol. 15, No. 3, pp. 223-228, Sep. 2008.

(Continued)

*Primary Examiner* — Charles A Marmor, II
*Assistant Examiner* — Thaddeus Cox
(74) *Attorney, Agent, or Firm* — McCarter & English, LLP

(57) ABSTRACT

A device that can be delivered into a body cavity to manipulate tissue intracorporeally while being controlled extracorporeally and a method of using the device to perform a single-port laparoscopic or natural orifice surgery are provided. The device is capable of being passed through an interior diameter of a single port into the body cavity. The device may include an anchor or suspension element that is attachable or mountable to the tissue intracorporeally, a guide element attached to the anchor or suspension element that allows for manipulation of at least one structure in at least one direction, and at least one structure attached to a suture or thread that is passable through the interior diameter of the port and positionable by the guide element. The structure is controllable extracorporeally by manipulating the suture or thread so that the structure moves in at least one direction intracorporeally.

10 Claims, 13 Drawing Sheets

(51) Int. Cl.

| | | |
|---|---|---|
| A61B 18/14 | (2006.01) | |
| A61B 18/18 | (2006.01) | |
| A61B 17/04 | (2006.01) | |
| A61B 17/06 | (2006.01) | |

(52) U.S. Cl.
CPC ..... *A61B 18/18* (2013.01); *A61B 2017/00212* (2013.01); *A61B 2017/00283* (2013.01); *A61B 2017/00876* (2013.01); *A61B 2017/0225* (2013.01); *A61B 2017/0464* (2013.01); *A61B 2017/0608* (2013.01)

(56) References Cited

U.S. PATENT DOCUMENTS

| | | | |
|---|---|---|---|
| 5,415,666 | A | 5/1995 | Gourlay et al. |
| 6,358,196 | B1 | 3/2002 | Rayman |
| 6,440,061 | B1 | 8/2002 | Wenner et al. |
| 7,270,672 | B1 | 9/2007 | Singer |
| 7,691,103 | B2 | 4/2010 | Fernandez et al. |
| 8,827,891 | B2 | 9/2014 | Roberts |
| 2002/0049367 | A1 | 4/2002 | Irion et al. |
| 2004/0034345 | A1 | 2/2004 | Lentz |
| 2004/0050395 | A1 | 3/2004 | Ueda et al. |
| 2004/0111100 | A1 | 6/2004 | Benderev et al. |
| 2005/0251207 | A1 | 11/2005 | Flores et al. |
| 2006/0149135 | A1 | 7/2006 | Paz |
| 2006/0217681 | A1 | 9/2006 | Hart et al. |
| 2007/0156028 | A1 | 7/2007 | Van Lue et al. |
| 2008/0027476 | A1 | 1/2008 | Piskun |
| 2009/0043246 | A1 | 2/2009 | Dominguez |
| 2009/0131749 | A1 | 5/2009 | Ahmed et al. |
| 2009/0326518 | A1 | 12/2009 | Rabin |
| 2010/0081875 | A1 | 4/2010 | Fowler et al. |
| 2010/0081880 | A1 | 4/2010 | Widenhouse et al. |
| 2010/0094227 | A1 | 4/2010 | Albrecht et al. |

FOREIGN PATENT DOCUMENTS

| | | |
|---|---|---|
| WO | WO 2008/045940 | 4/2008 |
| WO | WO 2010/042913 | 4/2010 |

OTHER PUBLICATIONS

Choi et al, Emerging Technologies—Single-Incision Laparoscopic Surgery: How and Why?, Bariatric Times, Apr. 2009.

Raman et al., Role of Magnetic Anchors During Laparoendoscopic Single Site Surgery and Notes, Journal of Endourology, vol. 23, No. 5, pp. 781-786, May 2009.

Dominguez et al., Retraction and Triangulation with Neodymium Magnetic Forceps for Single-Port Laparoscopic Cholecystectomy, Surg. Endosc, vol. 23, pp. 1160-1666, May 2009.

Chow et al., Single-Incision Laparoscopic Surgery for Cholecystectomy: An Evolving Technique, Surg. Endosc, vol. 24, pp. 709-714, Aug. 2009.

Single Port Approach to Surpass 20% of All Laparoscopic Procedures by 2014, PR Newswire, (No date).

PCT International Search Report and Written Opinion for PCT/US2008/009530 dated Feb. 2, 2009.

European Search Report of European Application No. 08827410.5 dated Jul. 9, 2012.

PCT/US2008/009530, filed Aug. 8, 2008, WO 2009/023136.

\* cited by examiner

O-Polysorb stitch is being placed to anterior abdominal wall for the creation of the loop to the anterior abdominal wall to be used as pulley.

Appendix is getting caught by Surgitie™ for later retraction.

The attached string to appendix will be pulled thru loop and subsequently thru the port to allow for retraction of the appendix.

Appendix is pulled to abdominal wall to expose the base of the appendix for dissection.

Ligation at base of appendix with Surgitie™.

Appendix is being transected.

Appendix is being placed in EndoCatch™ bag for retrieval.

SUSPENSION/RETRACTION DEVICE FOR SURGICAL MANIPULATION

CROSS REFERENCE TO RELATED APPLICATIONS

The present application is a continuation application that claims the benefit of a U.S. Non-Provisional (Rule 371) patent application Ser. No. 12/733,095, filed May 10, 2010, which claimed the benefit of PCT/US2008/009530, filed Aug. 8, 2008, which in turn claimed the benefit of U.S. Provisional Patent Application No. 60/964,319, filed on Aug. 10, 2007, and U.S. Provisional Patent Application No. 61/060,970, filed on Jun. 12, 2008, the subject matter of each of which is herein incorporated by reference in its entirety.

STATEMENT OF GOVERNMENT RIGHTS

This invention was made with government support under RR024139 awarded by the National Institutes of Health. The government has certain rights in the invention.

FIELD OF THE INVENTION

The present invention relates generally to an improved device for performing laparoscopic surgery and a method of using such a device to perform a single-port surgery.

BACKGROUND OF THE INVENTION

Laparoscopic surgery (which is also known as minimal invasive surgery (MIS)) has become increasingly popular over the last few years due to its benefits, including lower morbidity, less perceived pain, better cosmetic results and less hospital time. Laparoscopic surgery is one of the most commonly performed minimally invasive surgeries worldwide. Since its beginning, the advantages over an open surgical approach include, decreased pain, fewer postoperative complications, decreased length of hospitalization, better intra-abdominal visualization and better cosmetics are widely known and appreciated.

In laparoscopic surgery, small incisions, typically about 5 to about 15 millimeters in length, are made in the abdominal wall for the insertion of trocar ports (or other similar devices), which are thin tubes that span the thickness of the abdominal wall and allow for the insertion and extraction of the tools needed to perform the surgery.

In order to perform the surgery, the abdominal wall is pressurized with a gas (carbon dioxide) to a pressure of between about 10 and about 20 mm Hg to create a working space between the internal organs and the peritoneum. Typically the first tool introduced into and the last tool to be extracted from the abdominal cavity is an endoscope with its built in light source. The endoscope sends video images to a monitor that is used by the surgeon and medical staff to watch the introduction of other tools and, to make sure that such tools are properly introduced with no or minimal tissue damage.

In most laparoscopic surgeries, there are typically at least three tools that are required to perform the surgery—an endoscope, a grasper or lifter, and a cutting tool, which may be a scissor tool or electro-cautery. Furthermore, in a traditional laparoscopic surgical process, each tool that is needed/used requires its own trocar port. In addition, if access to a particular location is not possible from a current port, either a new port must be inserted or the tool in one of the other ports must be removed and then reinstalled.

There is always a risk of puncturing vital organs or blood vessels during the insertion of the trocar ports. Also, the repositioning of tools or the insertion of another port can result in a delay in the progress of the surgery, causing the patient to be under anesthesia for longer time periods and causing delays for the surgeon.

In the case of laparoscopic appendectomies, the classic laparoscopic technique typically utilizes three ports, which most commonly include one 12 mm and two 5 mm ports. The first port allows a laparoscope for visualization, the second harbors an instrument for dissection and the last port facilitates the use of an instrument for retraction of the appendix.

Over the past few years efforts have been made to reduce the number of ports required from three to two ports, or even a single port, and two-port techniques, hybrid approaches, and single-port assisted techniques have been developed in this regard. The two-port appendectomy technique is very similar to the standard three-port technique with the exception of one port allowing access for a rigid endoscope with a working channel and a second port that is used for a grasping instrument to provide retraction of the appendix.

In the hybrid technique, laparoscopy is combined with standard open techniques and the appendix is pulled out through the umbilicus in children or a right lower quadrant incision in adults to perform a traditional open appendectomy extracorporeally. The hybrid technique in which the appendix is pulled through a single incision in the umbilicus is only possible in the pediatric population because of the close proximity of the appendix and the umbilicus.

The single-port assisted technique uses one rigid endoscope with a working channel. The third port usually required for the retraction of the appendix is replaced by a sling suture that is put through the anterior abdominal wall in the right lower quadrant. The sling is then utilized to pull the appendix to the abdominal wall in order to provide the tension needed to perform the appendectomy intracorporeally. However, in order to place the transabdominal sling suture, the skin must be transversed twice with a needle to elevate the appendix to the abdominal wall.

Thus, it would be desirable to provide an improved laparoscopic technique that reduces the number of ports needed to perform laparoscopic surgery.

In addition, recent advances in laparoscopic surgical techniques have also allowed certain laparoscopic surgeries to be performed intraluminally, i.e., where access is gained through a natural orifice such as the vagina, rectum or esophagus. Thus, it would also be desirable to provide an improved technique for performing laparoscopic surgery intraluminally through a natural orifice.

SUMMARY OF THE INVENTION

It is an object of the present invention to provide an improved technique for laparoscopic surgery that promotes faster healing, less pain and less infection.

It is another object of the present invention to provide a single-port surgical technique as compared to the multiple-port techniques used previously.

It is still another object of the present invention to provide a puppeteer technique that allows a structure to be moved intracorporeally in various directions by controlling or manipulating the structure extracorporeally.

In one embodiment, the present invention relates generally to a device that can be delivered into a body cavity to manipulate tissue intracorporeally while being controlled extracorporeally, said device being capable of being passed through an interior diameter of a port into the body cavity, said device comprising:

a) an anchor or suspension means, wherein said anchor or suspension means is attached or mounted adjacent to tissue intracorporeally;

b) a guide means attached to the anchor or suspension means, where said guide means allows for manipulation of at least one structure in at least one direction; and c) at least one structure attached to a suture or thread that is passable through the interior diameter of the port and positionable by the guide means;

wherein the anchor or suspension means and the guide means provide leverage for moving the structure intracorporeally; and wherein the structure is controllable extracorporeally by manipulating the suture or thread, whereby the structure moves in at least one direction intracorporeally.

In another embodiment, the present invention relates to a kit for performing a single-port laparoscopic or natural orifice surgery comprising a device that can be delivered into a body cavity through a single port to manipulate tissue intracorporeally while being controlled extracorporeally, said device being capable of being passed through the single port into the body cavity, said kit comprising:

a) optionally, a trocar port;

b) an anchor or suspension element capable of passing through an inner diameter of the port, wherein said anchor or suspension element is attachable or mountable adjacent to an inner wall of the body cavity;

c) a guide element attached to the anchor or suspension element, where said guide element allows for manipulation of at least one structure in at least one direction; and c) at least one structure attached to at least one suture that is passable through the inner diameter of the port and positionable in at least one direction by the guide element;

wherein the anchor or suspension element and the guide element provide leverage for moving the at least one structure intracorporeally within the body cavity; and wherein the at least one structure is controllable extracorporeally by manipulating the at least one suture, whereby the at least one structure moves in at least one direction intracorporeally within the body cavity.

In still another embodiment, the present invention relates generally to a method of performing a single-port laparoscopic or natural orifice surgery with a device comprising (i) an anchor or suspension element that is attachable or mountable to or mountable adjacent to an interior wall of the body cavity; (ii) at least one guide element attached to the anchor or suspension element, where said at least one guide element allows for manipulation of at least one structure in at least one direction; and (iii) at least one structure attached to at least one suture that is positionable in at least one direction by the guide element; wherein the device is capable of being delivered into a body cavity through a single port to manipulate tissue intracorporeally while being controlled extracorporeally, the method comprising the steps of:

a) making a single incision in the wall of the body cavity to create a single port through which the device is passed;

b) passing the anchor or suspension element through the interior diameter of the port and attaching the anchor or suspension element to or mounting the anchor or suspension element adjacent to the interior wall of the body cavity;

d) passing the at least one structure attached to the at least one suture through the at least one guide element; and e) controlling the at least one structure intracorporeally by manipulating the at least one structure extracorporeally, whereby the at least one structure moves in at least one direction intracorporeally within the body cavity;

wherein the anchor or suspension element and the guide element provide leverage for moving the at least one structure intracorporeally within the body cavity.

BRIEF DESCRIPTION OF THE FIGURES

For a fuller understanding of the invention, reference is made to the following description taken in connection with the accompanying figures, in which.

Also, while not all elements are labeled in each figure, all elements with the same reference number indicate similar or identical parts.

DETAILED DESCRIPTION OF THE PREFERRED EMBODIMENTS

Figure 1:
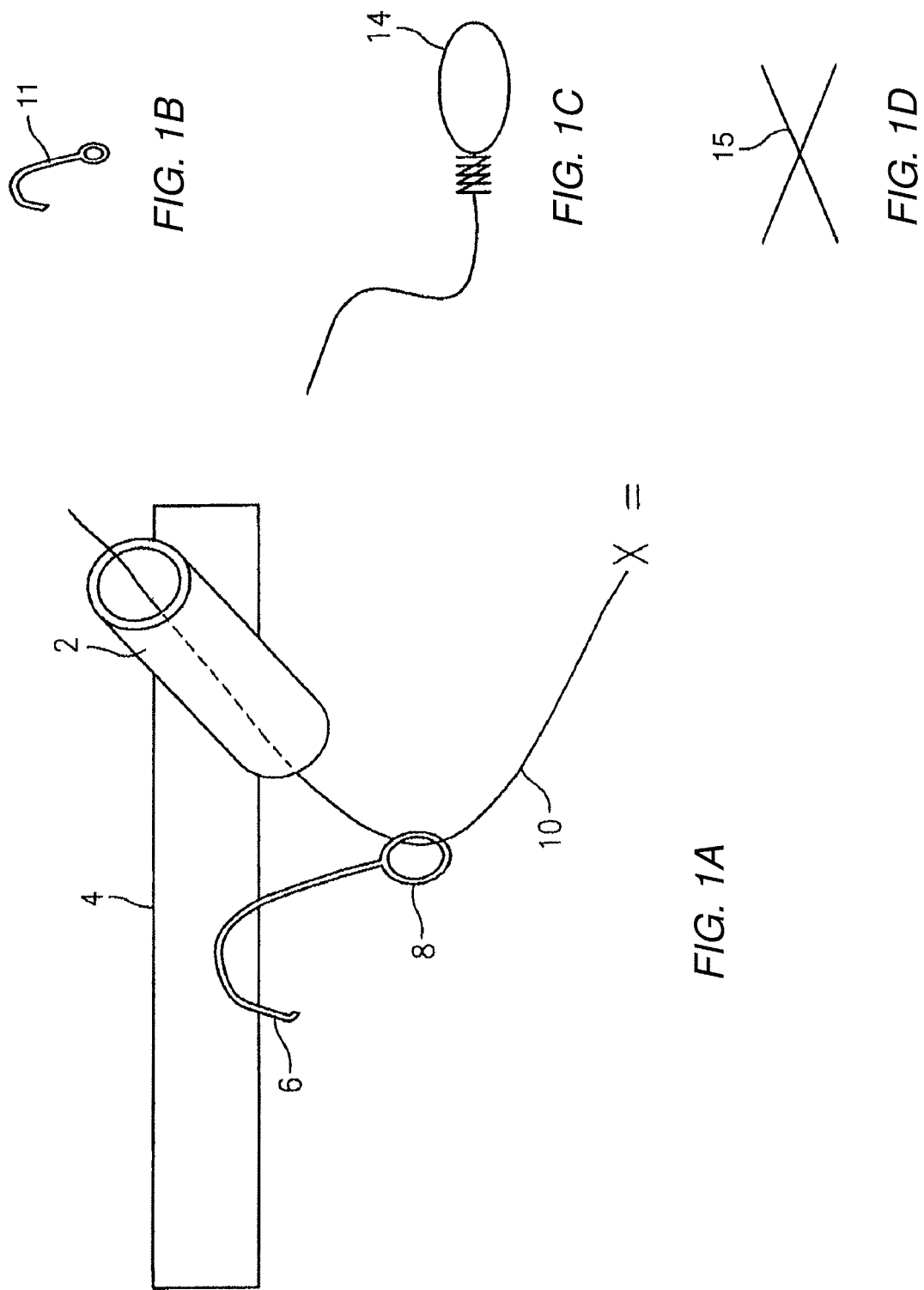
FIG. 1A depicts a device that can be delivered into a body cavity in which the guide means comprises a loop in accordance with a first embodiment of the invention.
FIG. 1B schematically depicts an exemplary hook for use with a first embodiment of the invention.
FIG. 1C schematically depicts an exemplary noose for use with a first embodiment of the invention.
FIG. 1D schematically depicts an exemplary grasper for use with a first embodiment of the invention.

The present invention relates generally to a device that can be delivered into a body cavity to manipulate tissue intracorporeally while being controlled extracorporeally. In one embodiment, the device may be wirelessly controlled extracorporeally. The device is designed to be capable of being passed through an interior diameter of an incision (port) into the body cavity.

The present invention relates generally to a laparoscopic technique that uses a single port without the need for any additional skin incisions or transdermally traversing needles and that is performed entirely intracorporeally. In addition, in one embodiment, the present invention allows the single incision to be placed anywhere on the abdominal wall to provide, the ability to hide the resulting scar in the umbilicus or in the suprapubic hairline. It can be desirable for cosmetic reasons to move laparoscopic incisions to hide them in the suprapubic hairline by decreasing the length of the incisions visible on the anterior abdominal wall.

The single-port technique of the invention is usable to perform various laparoscopic procedures including laparoscopic exploration, laparoscopic cholecystectomy, laparoscopic common bile duct exploration, laparoscopic drainage of pancreatic pseudocysts, laparoscopic distal pancreatectomy, laparoscopic appendectomy, laparoscopic hernia repair, laparoscopic hiatal hernia repair, laparoscopic lumbar hernia repair, laparoscopic gastric bypass, laparoscopic splenectomy, laparoscopic Nissen fundoplication, laparoscopic Heller myotomy, laparoscopic left and right hemicolectomies, laparoscopic abdominal-perineal resection, laparoscopic Ripsten procedure, laparoscopic reversal of colostomy, laparoscopic adrenalectomy, laparoscopic nephrectomy, laparoscopic nephroureterectomy, laparoscopic pyeloplasty, laparoscopic prostatectomy, laparoscopic feeding jejunostomy, laparoscopic small bowel resection, laparoscopic gastro-entero anastomosis, laparoscopic gastrectomy, laparoscopic repair of duodenal ulcer, laparoscopic liver resection, laparoscopic hepatic artery balloon pump placement, laparoscopic tumor staging, laparoscopic anterior spinal fusion, laparoscopic exploration of chronic abdominal pain, laparoscopic placement of peritoneal dialysis catheter, laparoscopic esophagectomy, laparoscopic procedures for treatment of infertility related to polycystic ovarian syndrome, laparoscopic pelvic lymph node sampling, among others, given by way of example and not limitation.

The single-port technique of the invention generally employs an innovative "puppeteer technique" which utilizes a pulley or other means of providing leverage in the intra-abdominal cavity. In one embodiment, the pulley is in the form of an intraabdominally placed loop that is used as an axle to elevate the appendix to the abdominal wall with a string. In a manner similar to a puppeteer moving the limbs of his puppet(s) with a string, the surgeon pulls this string extracorporeally, which moves and retracts the appendix, by way of example and not limitation, to the abdominal wall. Thus, in most instances, no further incisions, ports, or transdermally traversing needles are needed. If necessary however, such as if complications arise, a second port may be used to assist in the surgery.

In one embodiment, the device comprises:

a) an anchor or suspension means or element, wherein said anchor or suspension means or element is attached or mounted adjacent to tissue intracorporeally;

b) a guide means or element attached to the anchor or suspension means or element, where said guide means or element allows for manipulation of at least one structure in at least one direction; and c) at least one structure attached to a suture or thread that is passable through the interior diameter of the port and positionable by the guide means or element;

wherein the anchor or suspension means or element and the guide means or element provide leverage for moving the structure intracorporeally; and wherein the structure is controllable extracorporeally by manipulating the suture or thread, whereby the structure moves in at least one direction intracorporeally.

In one embodiment, the body cavity is an abdomen and said anchor or suspension means or element is intracorporeally attached to or mounted adjacent to an intraabdominal wall.

An example of a first embodiment of the device of the invention is depicted in FIGS. 1A-ID which shows a port 2 inserted into tissue 4. A hook 6 is used as the anchor or suspension means and is attached to a loop 8 which is used as the guide means. A structure X, which is attached to a suture 10 is then threaded through the loop 8 and is usable in the surgical procedure. In this example, X can be a hook 11, a noose 14 or a clamp or grasper 15.

The anchor or suspension means 6 can be any means that would be known to those skilled in the art for anchoring to tissue within the abdominal cavity. For example, the anchor or suspension means 6 may comprise at least one suture or at least one hook that is stitched or hooked into an intra-abdominal wall. In another embodiment, the anchor or suspension means 6 may comprises a plurality of magnets. In this embodiment, a corresponding plurality of magnets is provided extracorporeally to provide the magnetic force to hold the guide means or element, which is attached to the anchor or suspension means or element, in place intracorporeally.

Figure 5:
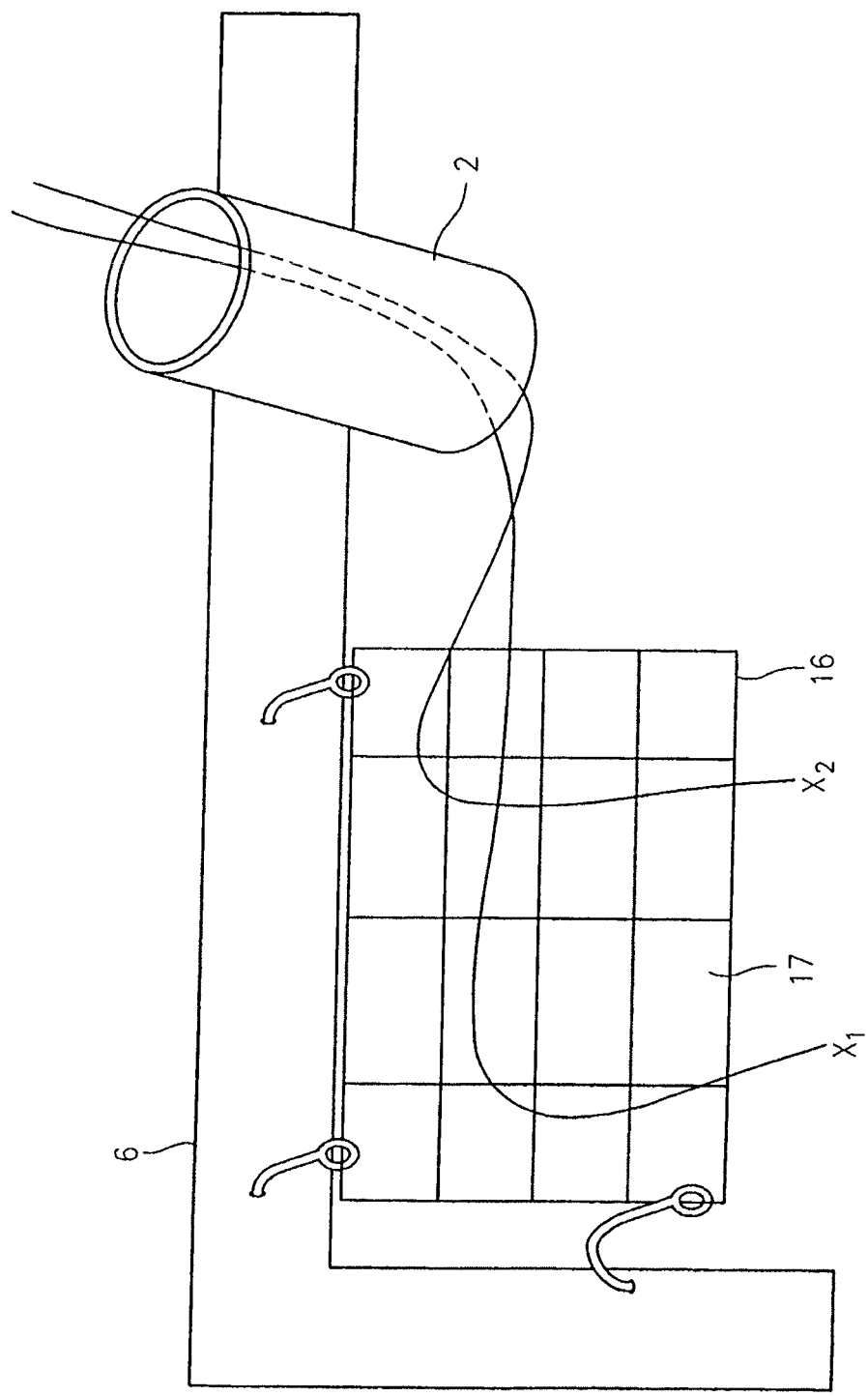
FIG. 5 depicts a device that can be delivered into a body cavity in which the guide means comprises an openwork grid in accordance with another embodiment of the invention.

The guide means can be any of a number of elements that are used to provide guidance and leverage to the at least one structure that is introduced through the port and into the body cavity. Examples of guide means that are usable in the practice of the invention include, for example, at least one of a loop 8, an elongated member 12 (depicted in FIG. 3) and an openwork grid 16 (depicted in FIG. 5). The guide means can be constructed of various materials, including for example, metals such as stainless steel and aluminum, various plastics, organic materials, natural and synthetic textiles, glass, and biodegradable materials, by way of example and not limitation.

In one embodiment, and as depicted in FIGS. 1A-1D, the guide means or element is a loop 8 and the structure X with the suture 10 attached thereto is threaded through the loop 8. The loop 8 then acts as a fulcrum to create intra-abdominal tension and countertension to control the structure intracorporeally by manipulating the suture 10 extracorporeally, i.e., the structure X is a puppet that is manipulated by the string (suture). In another embodiment, the structure can be controlled intracorporeally by wireless means extracorporeally.

Figure 3:
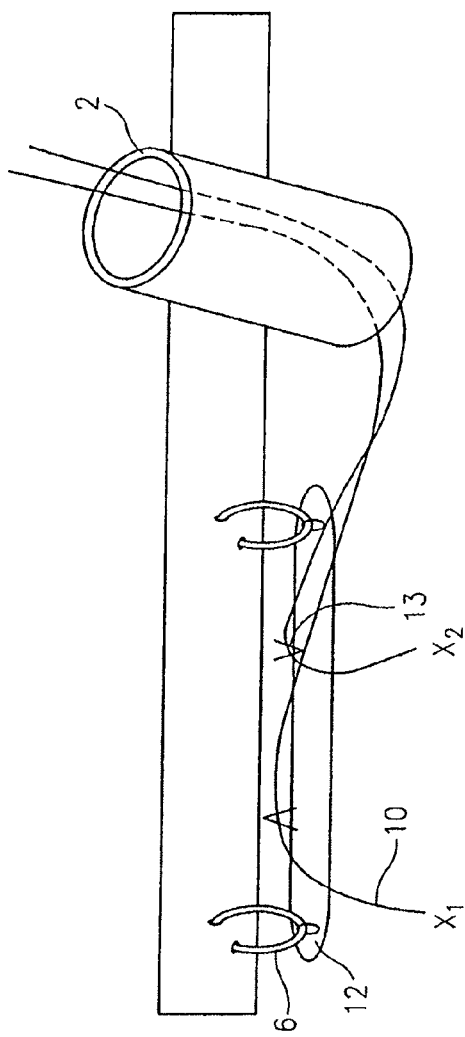
FIG. 3 depicts a device that can be delivered into a body cavity in which the guide means comprises an elongated rigid member in accordance with another embodiment of the invention.
Figure 4:
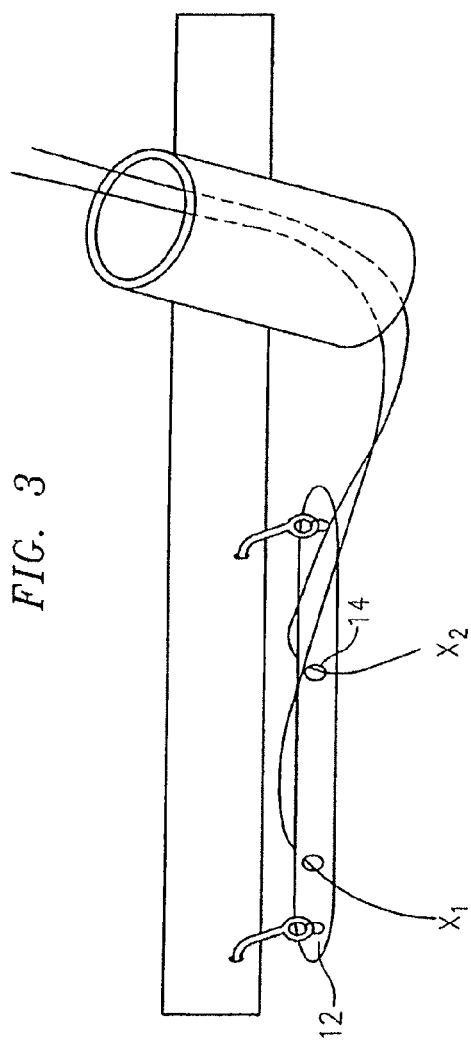
FIG. 4 depicts a variation of the elongated rigid member guide means depicted in FIG. 3.

In another embodiment, as depicted in FIG. 3, the guide means or element is a semi-rigid elongated member 12 that has sufficient flexibility to bend without breaking. The elongated member 12 typically has one or more notches 13, one or more hooks, one or more loops 14 (depicted in FIG. 4), or other such "guiding" features mounted thereon or holes drilled therethrough so that the structure X can be threaded through the notches, hooks, loops or holes, to guide the structure X within the abdomen or body cavity and provide leverage to the structure as discussed above.

Figure 6A:
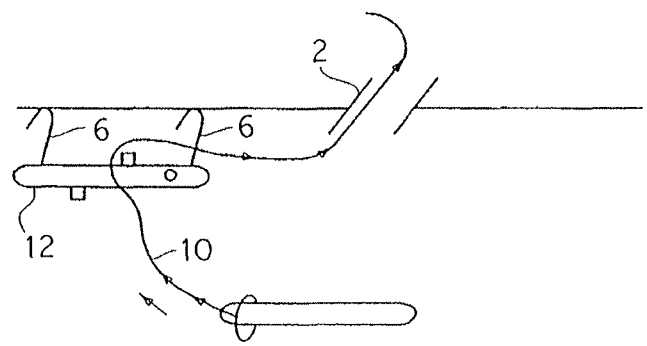
FIG. 6A depicts a variation of the elongated rigid member having telescoping portions.
Figure 6B:
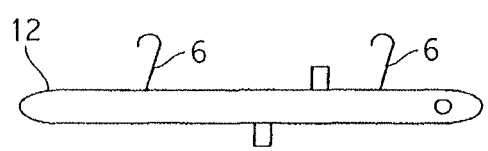
FIG. 6B depicts a portion of the variation depicted in FIG. 6A.
Figure 6C:
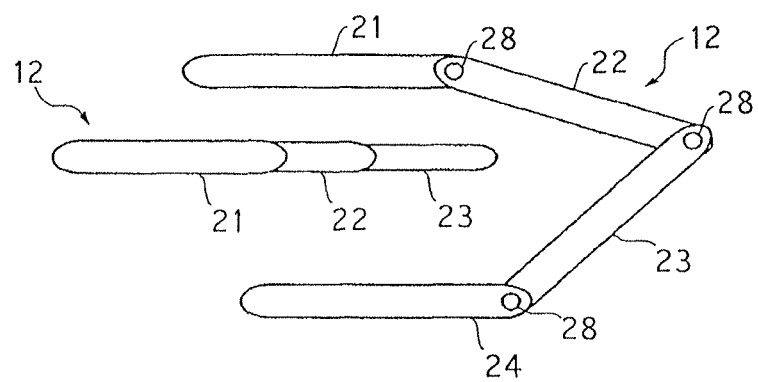
FIG. 6C is a further depiction of the variation of the elongated rigid member of FIG. 6A.

If desired, the elongated member 12 may comprise two or more rigid flexible portions as depicted in FIGS. 6A-6C. FIG. 6C depicts four portions 21, 22, 23 and 24 that are connected by means of joints or connectors 28. Thus the two or more portions 21, 22, 23, 24 can be folded onto one another to reduce the size of the elongated member 12 and facilitate easy entry and removal of the elongated member into and out of the body cavity. Furthermore, once the elongated member 12 is positioned within the body cavity and the first portion 21 is attached or mounted adjacent to the inner wall of the body cavity, the other portion(s) 22, 23 and 24 can be manipulated by the one or more sutures attached thereto to telescope the remaining portions into a desired position within the body cavity. In addition, these additional portions 22, 23, 24 can be sutured or otherwise attached to an inner wall of the body cavity to provide additional stability. Furthermore, while four portions are shown in FIG. 6C, the invention is not limited to four portions and may include as few as two and additional portions as needed to properly position the elongated member 12 within the body cavity.

In another embodiment of the invention, the guide means or element is an openwork grid 16 that is mounted substantially flush to a surface of the tissue with the anchor or suspension means. The openwork grid 16 comprises a plurality of openings 17 through which the at least one structure X is passed or guided. The openwork grid 16 can be introduced through the port by rolling the grid into the shape of a cylinder which is then unrolled once it is within the body cavity and is secured to the wall of the body cavity in several places. The openwork grid 16 can then be removed in a similar manner once surgery is completed, i.e., by rolling the grid 16 back into the shape of a cylinder.

The structure that is introduced into the abdomen can be any of a number of devices that are needed to perform various types of laparoscopic or other natural orifice or minimally invasive surgeries. For example, the structure can be selected from the group consisting of a noose, a bag, a receptacle, a hook, a grasper, a dissector, a manipulator, a clamp, a cutting implement, a scalpel, a scissors, a grabber, a lifter, a cauterizer, a dissector, an endoscope, a light or light delivery system, a sensor, an image sensor, a camera, including still and video cameras, a microrobot (such as described in U.S. Pat. No. 7,372,229 to Farritor et al., the subject matter of which is herein incorporated by reference in its entirety), and combinations of one or more of the foregoing. Other structures would also be known to those skilled in the art of particular laparoscopic, natural orifice and minimally invasive surgeries described herein and would be usable in the present invention.

Figure 2:
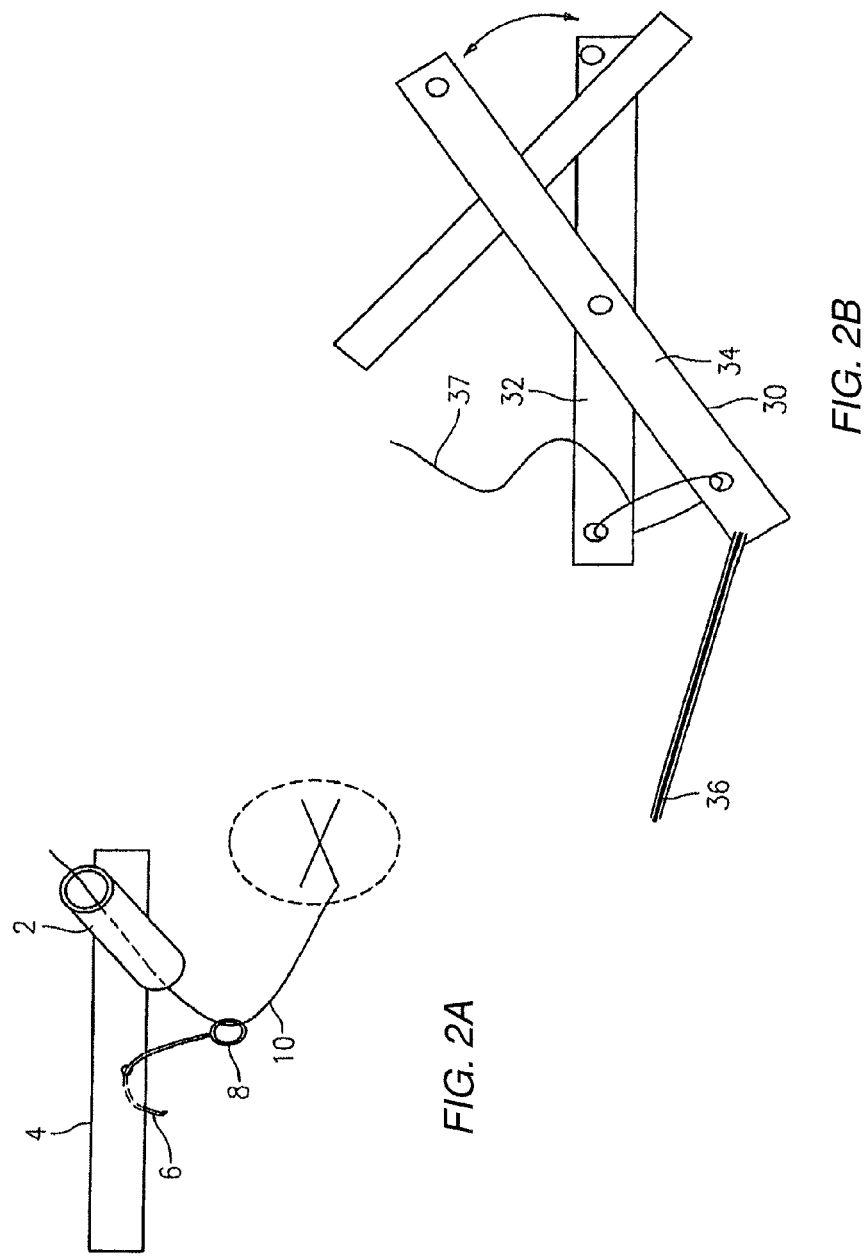
FIG. 2A depicts a device with a grasper or clamp in accordance with another embodiment of the invention.
FIG. 2B depicts an exemplary grasper or clamp in accordance with the embodiment FIG. 2A.

In one embodiment, as depicted in FIGS. 2A and 2B, the at least one structure is a grasper or clamp 25 having moveable pivotable blades or legs 32 and 34. This structure is then connected to one or more sutures 36 and 37 for manipulating the grasper or clamp 30. The structure may be tightened, released, or locked in place by manipulating the at least one suture 36 and 37 attached thereto. Thus the structure 30 may be tightened, and/or released and/or locked in place to grasp or clamp body tissue or may be locked in place or tightened to facilitate removal of the grasper or clamp through the port.

In one embodiment, the structures may be pre-strung on the suture to facilitate ease of use.

The present invention also relates to a kit for performing a single-port laparoscopic or natural orifice surgery comprising a device that can be delivered into a body cavity through a single port to manipulate tissue intracorporeally while being controlled extracorporeally, said device being capable of being passed through the single port into the body cavity.

The kit typically comprises:

a) optionally, a trocar port;

b) an anchor or suspension means or element capable of passing through an inner diameter of the port, wherein said anchor or suspension means or element is attachable or mountable adjacent to an inner wall of the body cavity;

c) a guide means or element attached to the anchor or suspension means or element, where said guide means or element allows for manipulation of at least one structure in at least one direction; and c) at least one structure attached to at least one suture that is passable through the inner diameter of the port and positionable in at least one direction by the guide means or element;

wherein the anchor or suspension means or element and the guide means or element provide leverage for moving the at least one structure intracorporeally within the body cavity; and wherein the at least one structure is controllable extracorporeally by manipulating the at least one suture, whereby the at least one structure moves in at least one direction intracorporeally within the body cavity.

In a preferred embodiment, the body cavity is the abdominal cavity and the kit contains structures needed for a performing a specific laparoscopic surgical procedures such as those defined above.

In another embodiment, the kit is designed for performing a laparoscopic appendectomy and the at least one structure comprises at least one of a noose, a bag, a receptacle, a hook, a clamp, scissors, a dissector, an instrument to facilitate removal of at least a portion the appendix, and other structures which may be used in performing a laparoscopic appendectomy.

In a preferred embodiment, the port through which the at least one structure is passable has an interior diameter of between about 5 and about 25 mm.

In another embodiment, the present invention relates to a method of performing a single-port laparoscopic surgery with a device comprising (i) an anchor or suspension element that is attachable or mountable to or mountable adjacent to an interior wall of the body cavity; (ii) at least one guide element attached to the anchor or suspension element, where said at least one guide element allows for manipulation of at least one structure in at least one direction; and (iii) at least one structure attached to at least one suture that is positionable in at least one direction by the guide element; wherein the device is capable of being delivered into an abdominal body cavity through a single port to manipulate tissue intracorporeally while being controlled extracorporeally, the method comprising the steps of:

a) making a single incision in the abdominal wall to create an opening in the abdominal wall through which the device is passed;

b) passing the anchor or suspension element through the interior diameter of the port and attaching the anchor or suspension element to or mounting the anchor or suspension element adjacent to the intra-abdominal wall;

c) passing the at least one structure attached to the at least one suture through the at least one guide element; and d) controlling the at least one structure intracorporeally by manipulating the at least one structure extracorporeally, whereby the at least one structure moves in at least one direction intracorporeally within the abdominal body cavity;

wherein the anchor or suspension element and the guide element provide leverage for moving the at least one structure intracorporeally within the abdominal cavity.

In a preferred embodiment, prior to step c) the abdominal cavity is insufflated to a suitable pressure. The insufflation is typically performed using carbon dioxide or another suitable fluid or inert gas.

The present invention also relates to a method of performing a single-port laparoscopic or natural orifice surgery with a device comprising (i) an anchor or suspension element that is attachable or mountable to or mountable adjacent to an interior wall of the body cavity; (ii) at least one guide element attached to the anchor or suspension element, where said at least one guide element allows for manipulation of at least one structure in at least one direction; and (iii) at least one structure attached to at least one suture that is positionable in at least one direction by the guide element; wherein the device is capable of being delivered into a body cavity through a single port to manipulate tissue intracorporeally while being controlled extracorporeally.

The method generally comprises the steps of:

a) making a single incision in the wall of the body cavity to create an opening through which the device is passed;

b) passing the anchor or suspension element through the interior diameter of the port and attaching the anchor or suspension element to or mounting the anchor or suspension element adjacent to the interior wall of the body cavity;

c) passing the at least one structure attached to the at least one suture through the at least one guide element; and d) controlling the at least one structure intracorporeally by manipulating the at least one structure extracorporeally, whereby the at least one structure moves in at least one direction intracorporeally within the body cavity.

As discussed above, the anchor or suspension element and the guide element provide leverage for moving the at least one structure intracorporeally within the body cavity.

The puppeteer technique of the invention has been found to provide adequate retraction to allow for dissection, ligation and transaction of the appendix at its base with no or minimal difficulties as discussed below in Example 1.

EXAMPLE 1

Single-Port Laparoscopic Appendectomy Performed on 14 Patients

During the study period, 17 patients with appendicitis presented to Yale New Haven Hospital (YNHH) when the inventor of the present invention as the surgeon on call for the Emergency General Surgery Service. Three patients were excluded according to established exclusion criteria. Thirteen of the remaining fourteen patients (8 females and 5 males) underwent a successful single-port laparoscopic appendectomy as described herein. No major complications were observed. One minor intraoperative complication was observed, in which the suprapubic access could be not be established safely and therefore an additional 5 mm port was placed infraumbilically. The laparoscopic appendectomy was then completed with 2 ports without further complications. One minor post-operative complication was seen in which a patient developed postoperative urinary retention, which resolved within 24 hours. Pathological examination revealed acute appendicitis in all but one case, in which signs of chronic inflammation of the appendix was identified. The individual patient characteristics are summarized in Table 1.

TABLE 1

Individual Patient Characteristics

| Patient | Gender | Age | BMI[1] | Access | OR-Time (min.) | Complications |
|---|---|---|---|---|---|---|
| 1 | F | 22 | 25.3 | TU[2] | 115 | |
| 2 | M | 46 | 28.3 | TU | 123 | |
| 3 | M | 29 | 29.8 | TU | 92 | |
| 4 | M | 40 | 19.4 | TU | 67 | |
| 5 | F | 47 | 31.1 | TU | 84 | |
| 6 | F | 37 | 36.0 | TU | 63 | |
| 7 | F | 35 | 39.0 | TU | 74 | |
| 8 | F | 40 | 20.4 | SP[3] | 54 | |
| 9 | F | 29 | 32.4 | SP | 95 | Urinary retention |
| 10 | F | 33 | 29.0 | SP | 128 | |
| 11 | F | 22 | 23.4 | SP | 87 | |
| 12 | M | 25 | 20.5 | SP | 68 | Inability to gain access - converted to two-port appendectomy |
| 13 | M | 59 | 27.5 | TU | 77 | |
| 14 | M | 49 | 22.0 | TU | 79 | |
| | 61% F | 37.5 | | | | |

[1]Body mass index
[2]Transumbilical
[3]suprapubic

The patients were positioned in a steep Trendelenberg position and left side down to aid in the visualization of the inflamed appendix. One 11 mm trocar is then placed infraumbilically or alternatively in the suprapubic hairline, via the Versastep® Veress system (available from Covidien AG, North Haven, Conn.). After access was successfully gained, a 10 mm rigid endoscope with a 5 mm working channel (available from Karl Storz, Tuttlingen, Germany) was used for the majority of the surgery. Intermittently, a 5 mm, 30° angled endoscope was needed to allow for the use of a 5 mm Ligasure® device (available from Covidien AG, North Haven, Conn.) for dissection and coagulation of the mesoappendix. This step is important because the working channel of the endoscope is typically too narrow to allow for the use of the Ligasure® device through the working channel. However, if an endoscope with a large enough working channel was used, this step would likely not be needed.

Figure 7:
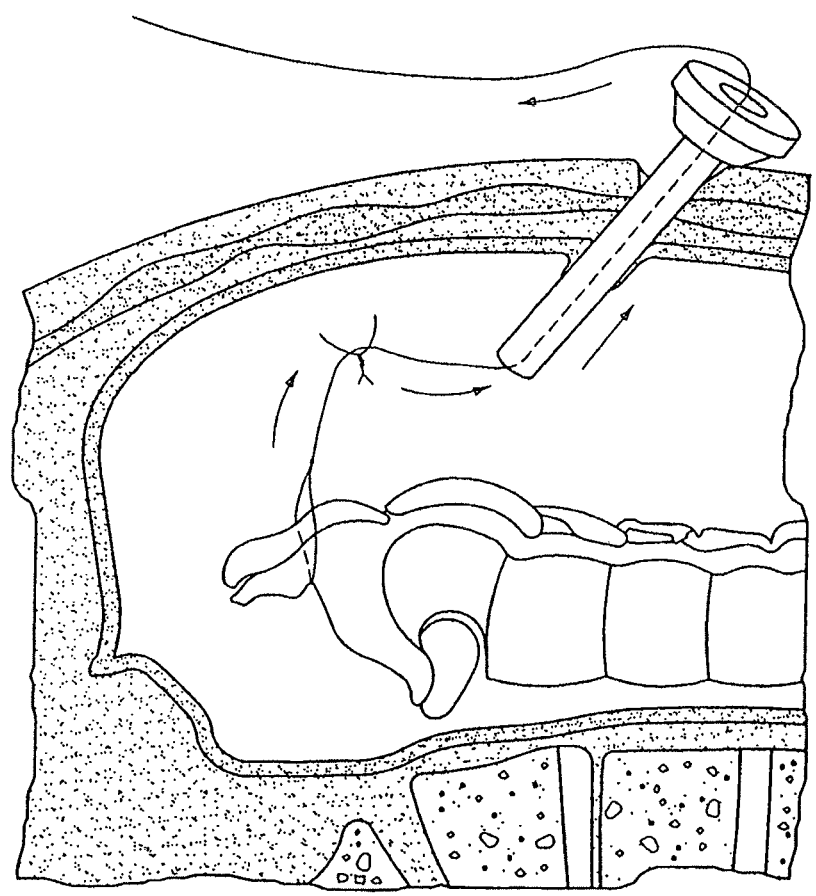
FIG. 7 depicts a basic principle of the novel technique of the invention as applied to a laparoscopic appendectomy.

Retraction for the ability to dissect between the appendiceal artery and the base of the appendix was achieved by pulling the appendix lateral, anterior and cephalad in the manner indicated in FIG. 7.

Figure 8:
FIG. 8 depicts a laparoscopic appendectomy performed in accordance with the present invention in which a 0-polysorb stitch is being placed to the anterior abdominal wall for the creation of the loop to be used as the guide means of the invention.

First, in order to achieve the fulcrum effect, a "pulley" was created by mounting a loop tied as an air knot (0-Polysorb®), available from Covidien AG, North Haven, Conn.) to the anterior abdominal wall within the abdominal cavity just cephalad and lateral to the base of the appendix. The loop is subsequently used as an axle as illustrated in FIG. 8.

Figure 9:
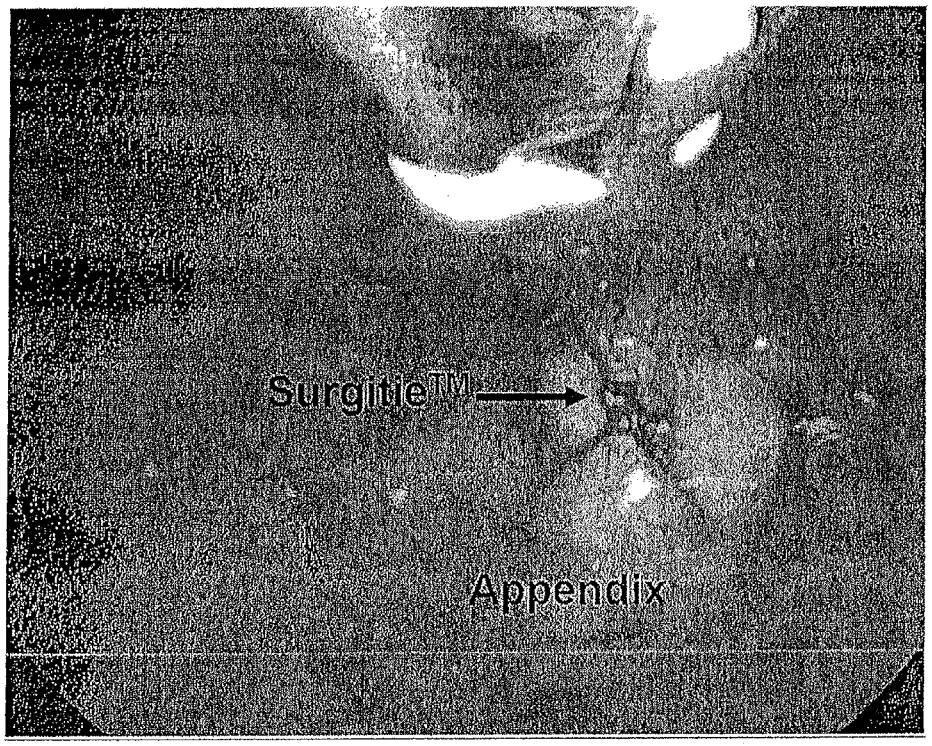
FIG. 9 depicts a laparoscopic appendectomy performed in accordance with the present invention in which the appendix is getting caught by Surgitie® for later retraction.
Figure 10:
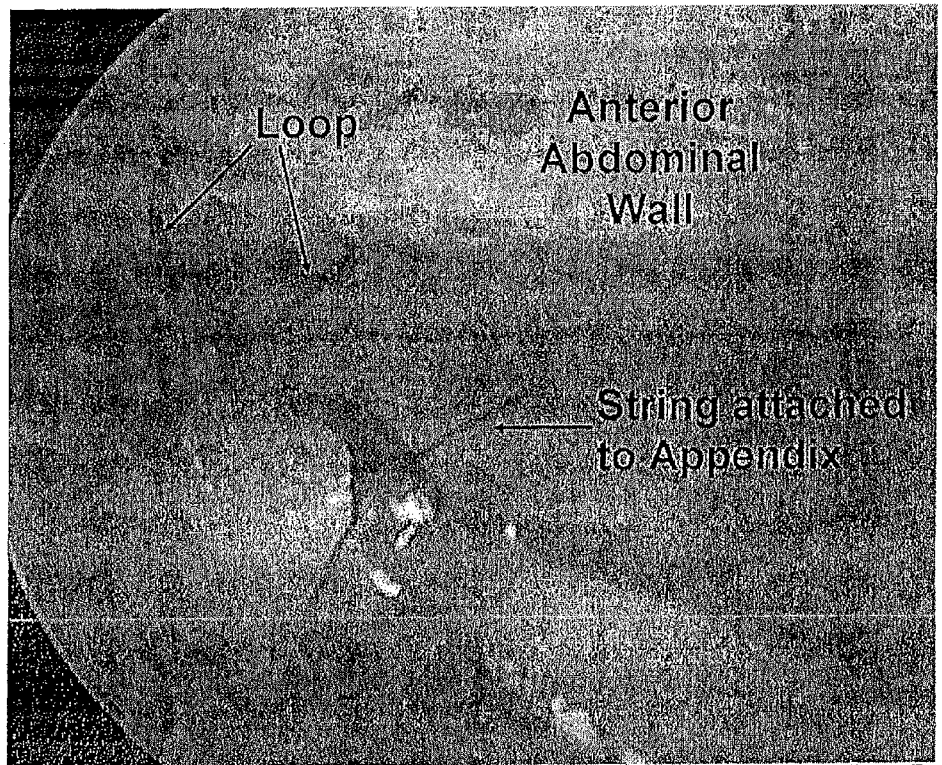
FIG. 10 depicts a laparoscopic appendectomy performed in accordance with the present invention in which the attached string/suture to the appendix is pulled through the loop and subsequently through the port to allow for retraction of the appendix.
Figure 11:
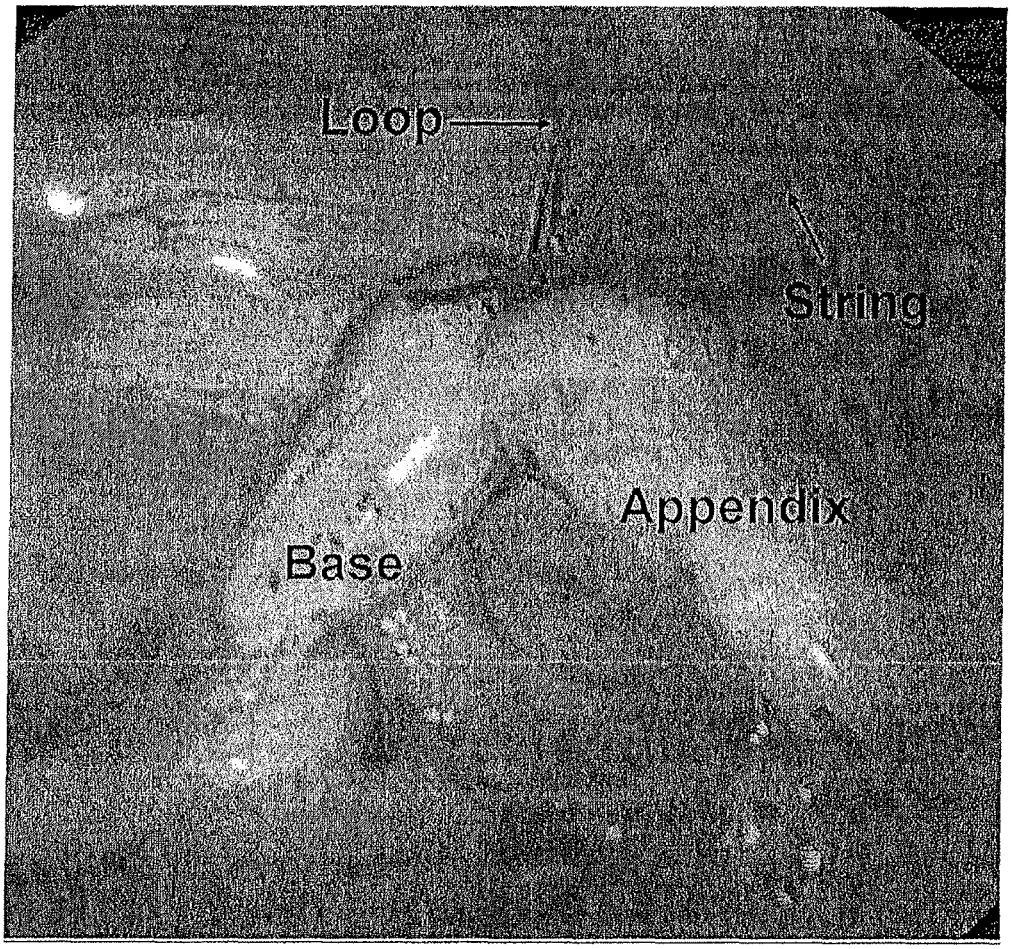
FIG. 11 depicts a laparoscopic appendectomy performed in accordance with the present invention in which the appendix is pulled to the abdominal wall to expose the base of the appendix for dissection.
Figure 12:
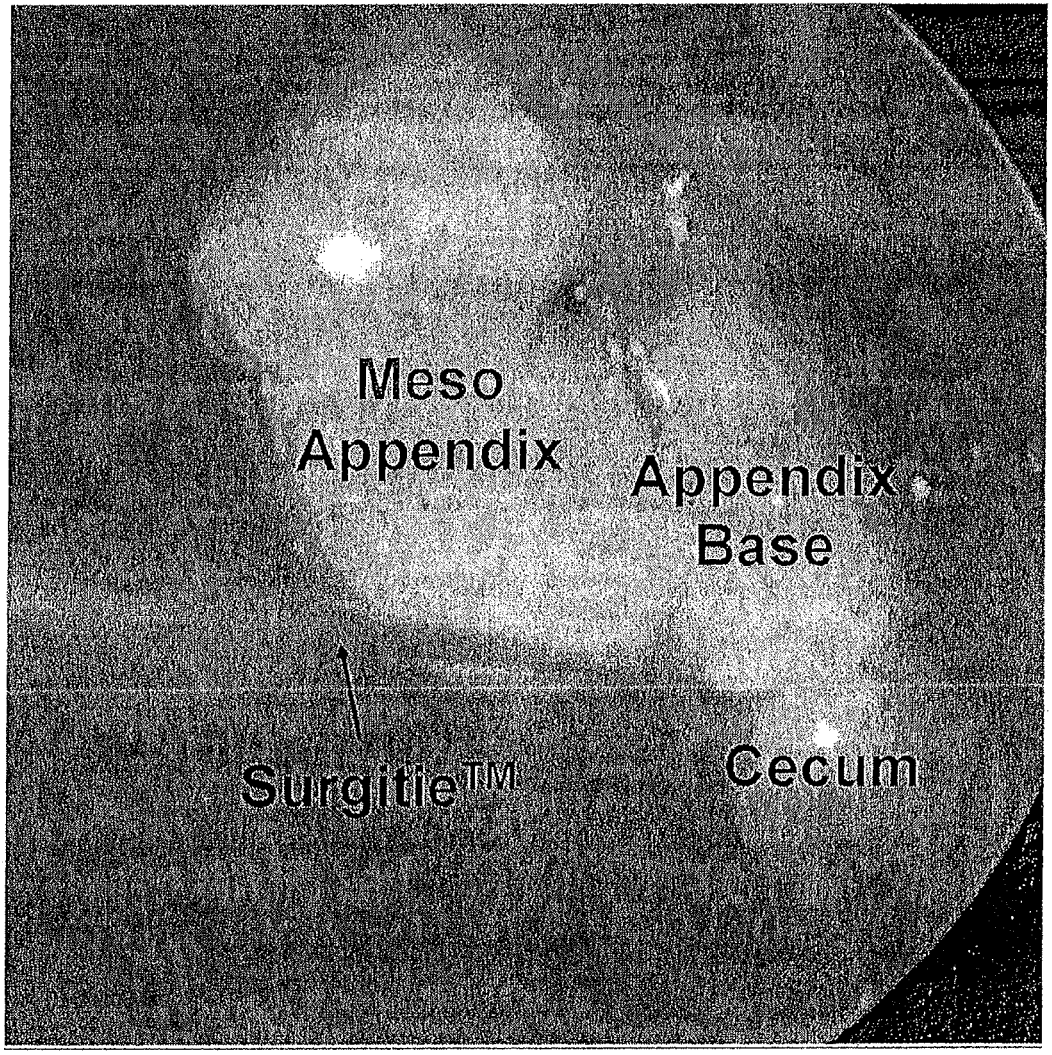
FIG. 12 depicts a laparoscopic appendectomy performed in accordance with the present invention in which ligation at the base of the appendix with Surgitie® is shown.

Next, a string (Surgitie®, available from Covidien AG, North Haven, Conn.) was placed around the appendix, as illustrated in FIG. 9. The string was threaded though the previously created loop and pulled through the 11 mm port to rest extracorporeally as illustrated in FIG. 10. This enabled the surgeon to pull on the string extracorporeally like a "puppeteer", which resulted in a lateral and anterior movement of the appendix to the abdominal wall, exposing the base of the appendix, as illustrated in FIG. 11. Then, the mesoappendix was dissected from the appendiceal base using a Maryland dissector. The Ligasure® device was used to seal and divide the mesoappendix, or a tie (0-Polysorb®) is used for ligation of the mesoappendix as depicted in FIG. 12.

Figure 13:
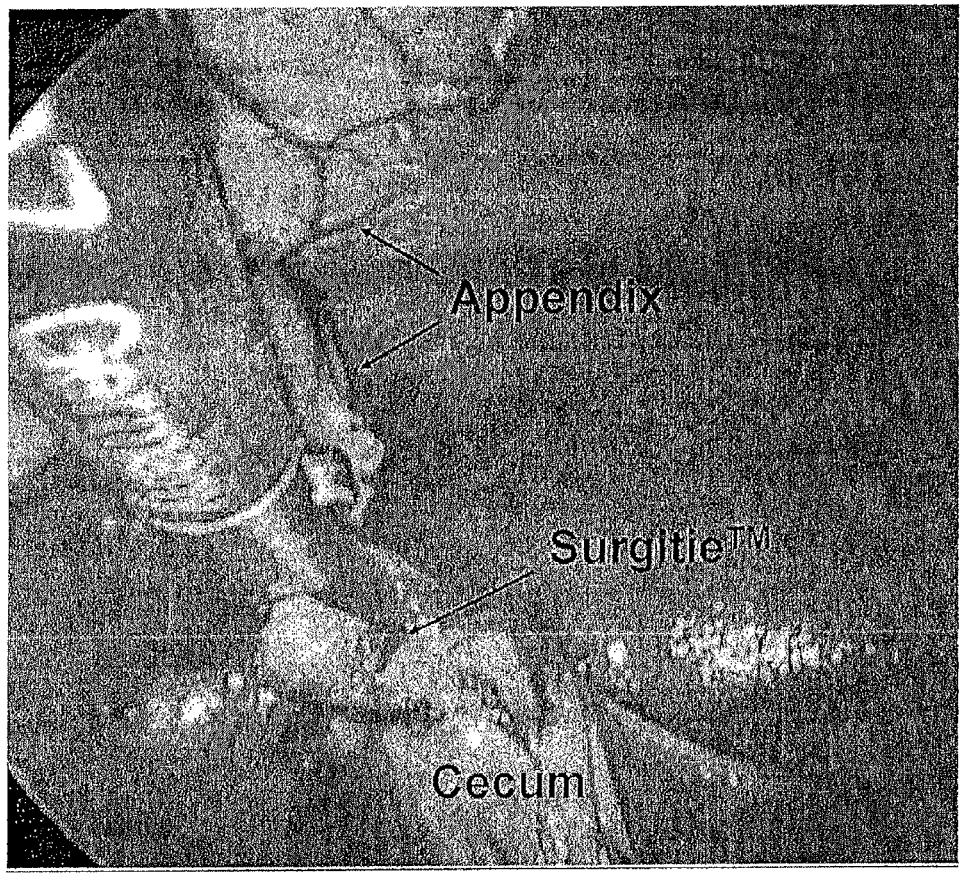
FIG. 13 depicts a laparoscopic appendectomy performed in accordance with the present invention in which the appendix is being transected.
Figure 14:
FIG. 14 depicts a laparoscopic appendectomy performed in accordance with the present invention in which the appendix is being placed in an EndoCatch® bag for retrieval.

Subsequently, another tie (0-Polysorb, available from Covidien AG, North Haven, Conn.) was placed around the appendix and divided using scissors, as illustrated in FIG. 13. The appendix was then placed in an EndoCatch® bag (available from Covidien AG, North Haven, Conn.) and retrieved from the patient's abdomen, as depicted in FIG. 14. The loop or "pulley" was then cut and removed. The 11 mm fascial defect was then closed with a 0-Polysorb statute in a FIG. 8 configuration. In the final step of the procedure, the skin was approximated with a simple interrupted 4-0 Caprosyn and Indermil® (available from Covidien AG, North Haven, Conn.) was applied.

As discussed above, the laparoscopic incision can be placed either transumbilically or in the suprapubic hairline. Applicant notes that the suprapubic approach has been associated with several complications due to following reasons. Firstly, there may be an inability to access the abdominal cavity safely, because of an incorrect insufflation and dissection with carbon dioxide of the preperitoneal space at the beginning of the operation which widened the space between the fascia and the peritoneum, and made a safe access difficult. Therefore, it may be necessary to use a primary transumbilical access. Secondly, another possible result of carbon dioxide dissection of the perperitoneal space my lead to postoperative urinary retention due to irritation of the bladder. Thus it is seen that both complications seem to be caused by preperitoneal insufflation with carbon dioxide. To avoid this problem, it may be preferred to use an open Hassan technique or another access method that provides visualization of the intraperitoneal space prior to insufflation with carbon dioxide which would prevent insufflation of the preperitoneal space with carbon dioxide.

While the example is shown as it relates to a laparoscopic appendectomy technique, the invention is not limited to appendectomies but is generally applicable to other laparoscopic and natural orifice surgery techniques that have previously required multiple ports to perform.

Finally, while the invention has been particularly shown and described with respect to preferred embodiments thereof, it will be understood that changes in form and details may be made therein without departing from the scope and spirit of the invention.

What is claimed is:

1. A system at least partially deliverable into a body cavity through an entry point, the system comprising:
   a) an anchor passable through the entry point, the anchor configured and dimensioned for attachment with respect to a first intracorporeal tissue at a location that is laterally spaced from the entry point;
   b) a suture disposed at least in part through the entry point and passing through the anchor, the suture defining an extracorporeal end portion and an intracorporeal end portion; and
   c) at least one tissue engaging structure associated with the intracorporeal end portion of the suture, the at least one tissue engaging structure configured and dimensioned for attachment to a second intracorporeal position;

wherein the suture defines three segments including (i) a first segment extending from an extracorporeal position relative to the entry point, through an interior passage associated with the entry point, and to an intracorporeal position, (ii) a second segment extending from the intracorporeal position to the anchor, and (iii) a third segment extending from the anchor to a second intracorporeal location, wherein the suture passes through the entry point and a guide element associated with the anchor defines a loop, a notch, a grid or a hook, and wherein pulling the suture extracorporeally away from the entry point causes the second intracorporeal location attached to the tissue engaging structure to be lifted towards the anchor.

2. The system according to claim 1, wherein the guide element is an elongated member that includes two or more portions that are connected by means of joints or connectors.

3. The system according to claim 2, wherein the two or more portions of the elongated member are folded onto one another to facilitate entry and removal of the elongated member.

4. The system according to claim 3, wherein at least a second portion of the elongated member is adapted for manipulation by the suture to telescope the second portion of the elongated member into a desired position.

5. The system according to claim 4, wherein the second portion of the elongated member is attached with respect to an inner wall of the cavity.

6. The system according to claim 1, wherein the guide element is a grid that is mounted substantially flush to an intracorporeal surface, said grid comprising a plurality of openings through which at least one structure may be passed or guided.

7. The system according to claim 6, wherein the at least one structure is selected from the group consisting of a noose, a bag, a receptacle, a hook, a grasper, a dissector, a manipulator, a clamp, a cutting implement, a scalpel, a scissors, a grabber, a lifter, a cauterizer, a dissector, an endoscope, a light or light delivery system, a sensor, an image sensor, a camera, including still and video cameras, a micro-robot and combinations of one or more of the foregoing.

8. The system according to claim 6, wherein the at least one structure is a grasper or clamp having pivotable blades or legs, wherein the at least one structure is connected to the suture, and wherein the grasper or clamp may be tightened, released or locked in place by manipulating the suture.

9. The system according to claim 6, wherein the at least one structure is pre-strung on the suture.

10. An intracorporeal surgical retraction system at least partially deliverable via an entry point, the system comprising:
    a) an anchor passable through the entry point, the anchor configured and dimensioned for attachment with respect to a first intracorporeal tissue at a location that is laterally spaced from the entry point;
    b) a suture disposed at least in part through the entry point and passing through the anchor, the suture defining an extracorporeal end portion and an intracorporeal end portion; and
    c) at least one tissue engaging structure associated with the intracorporeal end portion of the suture, the at least one tissue engaging structure configured and dimensioned for attachment to a second intracorporeal position;

wherein the suture passes through the entry point and a guide element associated with the anchor defines a loop, a notch, a grid or a hook, and wherein pulling the suture extracorporeally away from the entry point causes a second intracorporeal location attached to the surface engaging structure to be retracted towards the anchor, wherein the more the suture is pulled extracorporeally away from the entry point, the more the second intracorporeal position attached to the tissue engaging structure is retracted towards the anchor, thereby enabling dynamic retraction.

\* \* \* \* \*